US012729374B2

(12) United States Patent
Kim et al.

(10) Patent No.: US 12,729,374 B2
(45) Date of Patent: Sep. 8, 2026

(54) **GLYCOSYLTRANSFERASE AND *STEVIOL* GLUCOSIDE PREPARATION METHOD USING SAME**

(71) Applicant: SAMYANG CORPORATION, Seoul (KR)

(72) Inventors: Jeong Min Kim, Yongin-si (KR); Hyeok-Jin Ko, Seongnam-si (KR); Jun-Ho Moon, Seoul (KR); Eunsoo Choi, Seongnam-si (KR)

(73) Assignee: SAMYANG CORPORATION, Seoul (KR)

( * ) Notice: Subject to any disclaimer, the term of this patent is extended or adjusted under 35 U.S.C. 154(b) by 380 days.

(21) Appl. No.: 18/266,676

(22) PCT Filed: Dec. 23, 2021

(86) PCT No.: PCT/KR2021/019767

§ 371 (c)(1),
(2) Date: Jun. 12, 2023

(87) PCT Pub. No.: WO2022/139522

PCT Pub. Date: Jun. 30, 2022

(65) Prior Publication Data

US 2025/0320470 A1 Oct. 16, 2025

(30) Foreign Application Priority Data

Dec. 23, 2020 (KR) ........................ 10-2020-0182517

(51) Int. Cl.

| | |
|---|---|
| ***C12N 9/10*** | (2006.01) |
| ***C12N 15/70*** | (2006.01) |
| ***C12N 15/81*** | (2006.01) |
| ***C12P 19/56*** | (2006.01) |

(52) U.S. Cl.

CPC ........... *C12N 9/1051* (2013.01); *C12N 15/70* (2013.01); *C12N 15/81* (2013.01); *C12P 19/56* (2013.01)

(58) Field of Classification Search

CPC ...... C12N 9/1051; C12N 15/70; C12N 15/81; C12P 19/56

See application file for complete search history.

(56) References Cited

U.S. PATENT DOCUMENTS

| | | | | |
|---|---|---|---|---|
| 9,522,929 | B2 * | 12/2016 | Mao | C12N 9/1062 |
| 11,091,743 | B2 * | 8/2021 | Zhao | C12P 19/56 |
| 2020/0087692 | A1 | 3/2020 | Kumaran et al. | |
| 2025/0051818 | A1 * | 2/2025 | Ko | C12N 9/10 |
| 2025/0154549 | A1 * | 5/2025 | Kim | C12P 19/56 |

FOREIGN PATENT DOCUMENTS

| | | |
|---|---|---|
| JP | 2017-079739 | 5/2017 |
| KR | 10-2015-0000258 | 1/2015 |
| KR | 10-2016-0111998 | 9/2016 |
| KR | 10-2016-0116775 | 10/2016 |
| KR | 10-2017-0135848 | 12/2017 |
| WO | 2016054540 | 4/2016 |
| WO | 2018031955 | 2/2018 |
| WO | 2020123877 | 6/2020 |

OTHER PUBLICATIONS

Database GenPept [online]: Accession No. XP_037427692: UDP-glycosyltransferase 91C1-like [Triticum dicoccoides]. Nov. 13, 2020, total 2 pages.

KIPO, A PCT Search Report & Written Opinion of PCT/KR2021/019767 dated Apr. 5, 2022.

NCBI, GenBank Accession No. KAF7047425.1 “hypothetical protein CFC21_056359 [Triticum aestivum]”.

* cited by examiner

*Primary Examiner* — Ganapathirama Raghu

(74) *Attorney, Agent, or Firm* — LEX IP MEISTER, PLLC

(57) ABSTRACT

The present invention discloses a glycosyltransferase and a composition and method for producing steviol glycoside using the same, and more particularly, a glycosyltransferase of rebaudioside that transfers glucose to steviol glycoside, a recombinant strain expressing the enzyme, and a method of producing rebaudioside, a steviol glycoside, using the same.

7 Claims, 3 Drawing Sheets

Specification includes a Sequence Listing.

SEQUENCE LISTING

```
<160> NUMBER OF SEQ ID NOS: 16

<210> SEQ ID NO 1
<211> LENGTH: 461
<212> TYPE: PRT
<213> ORGANISM: Artificial Sequence
<220> FEATURE:
<223> OTHER INFORMATION: TaUGT amino acid sequence

<400> SEQUENCE: 1

Met Asp Asp Gly Ser Ser Ser Ser Ser Ser Pro Leu Arg Val Val Ile
1               5                   10                  15

Cys Pro Trp Leu Ala Phe Gly His Leu Leu Pro Cys Leu Asp Ile Ala
            20                  25                  30

Glu Arg Leu Ala Ser Arg Gly His Arg Val Ser Phe Val Ser Thr Pro
        35                  40                  45

Arg Asn Ile Ala Arg Leu Pro Pro Val Arg Pro Ala Val Ala Pro Leu
    50                  55                  60

Val Asp Tyr Val Ala Leu Pro Leu Pro Arg Val Asp Gly Leu Pro Glu
65                  70                  75                  80

Gly Ala Glu Ser Thr Asn Asp Val Pro His Asp Lys Phe Glu Leu Leu
                85                  90                  95

Arg Lys Ala Phe Asp Gly Leu Ala Ala Pro Phe Ser Glu Phe Leu His
            100                 105                 110

Ala Ala Cys Ala Glu Gly Thr Gly Lys Arg Pro Asp Trp Leu Ile Val
        115                 120                 125

Asp Ser Phe His His Trp Ala Ala Ala Ala Ala Val Glu Asn Lys Val
    130                 135                 140

Pro Cys Val Met Leu Leu Leu Gly Ala Ala Asn Val Ile Ala Thr Trp
145                 150                 155                 160

Ala Arg Gly Val Ser Glu His Ala Ala Ala Ala Val Gly Lys Glu Arg
                165                 170                 175

Ser Ala Ala Glu Ala Pro Ser Phe Glu Thr Glu Arg Arg Lys Leu Met
            180                 185                 190

Ile Thr Gln Asn Ala Ser Gly Met Thr Val Ala Glu Arg Tyr Phe Leu
        195                 200                 205

Thr Leu Met Arg Ser Asn Leu Val Ala Ile Arg Ser Cys Ala Glu Trp
```

```
    210                 215                 220

Glu Pro Glu Ser Val Ala Ala Leu Thr Thr Leu Ala Gly Lys Pro Val
225                 230                 235                 240

Val Thr Leu Gly Leu Leu Pro Pro Ser Pro Glu Gly Gly Arg Gly Ile
                245                 250                 255

Ser Lys Gln Asp Ala Ala Val Arg Trp Leu Asp Ala Gln Arg Asp Lys
            260                 265                 270

Ser Val Val Tyr Val Ala Leu Gly Ser Glu Val Pro Leu Arg Val Glu
        275                 280                 285

Gln Val His Glu Leu Ala Leu Gly Leu Glu Leu Ser Gly Ala Ser Phe
    290                 295                 300

Leu Trp Ala Leu Arg Lys Pro Pro Gly Met Pro Asp Ala Ala Val Leu
305                 310                 315                 320

Pro Pro Gly Phe Glu Glu Arg Thr Arg Gly Arg Gly Leu Val Val Thr
                325                 330                 335

Gly Trp Val Pro Gln Ile Ser Val Leu Ala His Gly Ala Val Ala Ala
            340                 345                 350

Phe Leu Thr His Cys Gly Trp Asn Ser Thr Ile Glu Gly Leu Leu Phe
        355                 360                 365

Gly Gln Pro Leu Ile Met Leu Pro Ile Ser Ser Asp Gln Gly Pro Asn
    370                 375                 380

Ala Arg Leu Met Glu Gly Arg Lys Val Gly Met Gln Val Pro Arg Asn
385                 390                 395                 400

Glu Ser Asp Gly Ser Phe Thr Arg Glu Asp Val Ala Ala Thr Val Gln
                405                 410                 415

Ala Val Ala Met Glu Glu Asp Gly Ser Arg Val Phe Thr Ala Asn Ala
            420                 425                 430

Lys Thr Met Gln Glu Ile Val Ala Asp Ser Ala Cys His Glu Arg Cys
        435                 440                 445

Ile Asp Gly Phe Ile Gln Gln Leu Arg Ser Tyr Lys Glu
    450                 455                 460


<210> SEQ ID NO 2
<211> LENGTH: 1383
<212> TYPE: DNA
<213> ORGANISM: Artificial Sequence
<220> FEATURE:
<223> OTHER INFORMATION: TaUGT nucleotide sequence

<400> SEQUENCE: 2

atggacgacg ggtcttctag ctctagcagt ccgctgcgtg ttgttatttg cccgtggctg     60

gcttttggac acctgcttcc atgcttagac attgcggaaa gattagccag ccgtggacac    120

agagtatcct tcgtaagtac gccgcgtaat atagcacgtt tacccccggt cagaccggca    180

gttgcgccgc tggtcgatta cgtagcgcta cctctgccca gagtggacgg acttccggaa    240

ggggctgaat ctacaaacga cgtgccccat gataagttcg agcttttacg taaggctttc    300

gacggtttgg cagcgccctt cagcgaattt ctacacgcag cgtgcgcgga gggcacaggc    360

aaaagaccag attggcttat tgtggattcc ttccaccatt gggctgcggc tgcggcagtg    420

gaaaataaag tcccgtgcgt catgttactt ttaggtgcag ccaacgtgat cgccacttgg    480

gcacgtggcg tgtcagagca tgcggccgcc gcggttggaa aagaacgtag tgccgcagaa    540

gctccatcat tcgaaaccga acgtcgtaaa ctgatgataa ctcagaatgc atcaggtatg    600

accgtagcag agcgttattt cctgacactt atgagatcaa acttggttgc cattcgttcc    660
```

-continued

```
tgtgcagaat gggagcctga atctgtggcg gcactaacca ctctggccgg gaagcccgta    720

gtgaccttag gtttgcttcc accgtctcct gagggaggaa ggggtatttc caagcaagac    780

gctgccgtta ggtggctgga cgctcagagg gataagtccg ttgtatacgt ggcgttaggg    840

tctgaagttc ccttgagagt ggagcaggta catgagcttg cgcttggact agagttgtca    900

ggtgctagct tcctgtgggc gttacgtaag ccacccggca tgcctgacgc cgcagtcttg    960

ccgccgggtt ttgaagagag aaccagggga cgtggtctgg ttgtgactgg ctgggtacca   1020

caaatcagcg tcttagcaca tggcgccgtt gccgcttttc tgacacattg cggctggaat   1080

agtacaatcg aaggcttgct gttcggacaa ccgttaatca tgctgccaat cagtagcgat   1140

cagggcccga atgcccgtct tatggaggga agaaaagttg gaatgcaggt gcctcgtaat   1200

gagtccgatg gatcattcac aagagaggat gtcgctgcca cagtacaagc agtagcgatg   1260

gaggaggatg ggagccgtgt ttttacggct aatgcaaaga ccatgcaaga aatagttgct   1320

gactccgcgt gtcacgaaag gtgcatcgat ggatttatcc aacagctaag gtcctataaa   1380

gaa                                                                 1383


<210> SEQ ID NO 3
<211> LENGTH: 462
<212> TYPE: PRT
<213> ORGANISM: Artificial Sequence
<220> FEATURE:
<223> OTHER INFORMATION: EUGT11 amino acid sequence

<400> SEQUENCE: 3

Met Asp Ser Gly Tyr Ser Ser Ser Tyr Ala Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
```

-continued

```
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
        275                 280                 285

Glu Lys Val His Glu Leu Ala Leu Gly Leu Glu Leu Ala Gly Thr Arg
    290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
        355                 360                 365

Phe Gly His Pro Leu Ile Met Leu Pro Ile Phe Gly Asp Gln Gly Pro
    370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
        435                 440                 445

Tyr Ile Asp Gly Phe Ile Gln Gln Leu Arg Ser Tyr Lys Asp
    450                 455                 460
```

```
<210> SEQ ID NO 4
<211> LENGTH: 1386
<212> TYPE: DNA
<213> ORGANISM: Artificial Sequence
<220> FEATURE:
<223> OTHER INFORMATION: EUGT11 nucleotide sequence

<400> SEQUENCE: 4

atggactccg gctacagttc atcatatgct gcagccgctg ggatgcacgt tgtgatttgt     60

ccgtggctag cattcggtca tctgttgccg tgtttggacc tggctcagag gctagcttcc    120

agaggacatc gtgtttcctt cgtttctacg cctaggaata tcagtagact accaccggta    180

agacctgctt tagctccact tgtggcgttc gtggccctac cgttaccccg tgtagaagga    240

ttgcctgacg gagcagagtc tacgaatgac gtacctcacg acagacccga tatggttgaa    300

cttcacagaa gagcgttcga cggtcttgct gcaccgtttt ccgaattcct tgggacggcc    360

tgtgcggact gggtcatagt ggacgtattc catcactggg ctgccgcagc tgccctagaa    420

cataaggttc cgtgtgccat gatgttgtta ggttctgctc atatgatcgc gtctattgca    480

gaccgtaggt tggagagggc agaaacggaa agtccagccg ccgccggaca ggggaggccc    540

gctgcggcgc caacctttga ggtggctcgt atgaaactaa ttaggactaa aggttcaagc    600

ggtatgtcac tggcggaaag gtttagtctt actttgtcca ggtcttcatt ggtcgtcggt    660

cgttcctgcg ttgagtttga acccgaaacc gttcccctc tttccacgtt acgtggaaaa    720

ccgattactt ttcttggtct tatgccgcca ctgcacgagg gtagaaggga agatggtgaa    780
```

-continued

```
gacgctacag ttaggtggct agacgcgcaa ccggctaaga gcgtcgtcta tgtcgcactt    840

ggctcagagg tgcccttggg ggtcgagaag gtccatgagt tggcgctggg gttggagttg    900

gcgggtacaa ggtttctttg ggcccttcgt aaaccgacgg gcgtatcaga tgcagaccta    960

cttccggctg gtttcgagga gcgtactagg ggaaggggcg ttgtggccac gagatgggtg   1020

ccacaaatga gcatcctagc tcatgccgca gtcggcgcat tcttaacgca ttgtggctgg   1080

aattcaacca ttgaagggct aatgttcggt catccactga taatgcttcc tatctttgga   1140

gaccaaggtc ccaatgcgcg tttgatcgaa gccaagaatg ctggccttca agtcgcccgt   1200

aatgatggcg atggttcatt cgacagagag ggagtggcgg cagcgatcag agcggttgca   1260

gtggaagagg agtccagtaa ggtgtttcag gctaaggcca agaaattaca ggagatagtg   1320

gctgatatgg cttgccacga gagatatatc gacggcttta tacaacagct acgttcttat   1380

aaggac                                                              1386
```

<210> SEQ ID NO 5
<211> LENGTH: 463
<212> TYPE: PRT
<213> ORGANISM: Artificial Sequence
<220> FEATURE:
<223> OTHER INFORMATION: HvUGT amino acid sequence

<400> SEQUENCE: 5

```
Met Asp Gly Asp Gly Asn Ser Ser Ser Ser Ser Ser Pro Leu His Val
1               5                   10                  15

Val Ile Cys Pro Trp Leu Ala Leu Gly His Leu Leu Pro Cys Leu Asp
            20                  25                  30

Ile Ala Glu Arg Leu Ala Ser Arg Gly His Arg Val Ser Phe Val Ser
        35                  40                  45

Thr Pro Arg Asn Ile Ala Arg Leu Pro Pro Leu Arg Pro Ala Val Ala
    50                  55                  60

Pro Leu Val Glu Phe Val Ala Leu Pro Leu Pro His Val Asp Gly Leu
65                  70                  75                  80

Pro Glu Gly Ala Glu Ser Thr Asn Asp Val Pro Tyr Asp Lys Phe Glu
                85                  90                  95

Leu His Arg Lys Ala Phe Asp Gly Leu Ala Ala Pro Phe Ser Glu Phe
            100                 105                 110

Leu Arg Ala Ala Cys Ala Glu Gly Ala Gly Ser Arg Pro Asp Trp Leu
        115                 120                 125

Ile Val Asp Thr Phe His His Trp Ala Ala Ala Ala Ala Val Glu Asn
    130                 135                 140

Lys Val Pro Cys Val Met Leu Leu Leu Gly Ala Ala Thr Val Ile Ala
145                 150                 155                 160

Gly Phe Ala Arg Gly Val Ser Glu His Ala Ala Ala Ala Val Gly Lys
                165                 170                 175

Glu Arg Pro Ala Ala Glu Ala Pro Ser Phe Glu Thr Glu Arg Arg Lys
            180                 185                 190

Leu Met Thr Thr Gln Asn Ala Ser Gly Met Thr Val Ala Glu Arg Tyr
        195                 200                 205

Phe Leu Thr Leu Met Arg Ser Asp Leu Val Ala Ile Arg Ser Cys Ala
    210                 215                 220

Glu Trp Glu Pro Glu Ser Val Ala Ala Leu Thr Thr Leu Ala Gly Lys
225                 230                 235                 240

Pro Val Val Pro Leu Gly Leu Leu Pro Pro Ser Pro Glu Gly Gly Arg
```

-continued

```
                245                 250                 255

Gly Val Ser Lys Glu Asp Ala Ala Val Arg Trp Leu Asp Ala Gln Pro
            260                 265                 270

Ala Lys Ser Val Val Tyr Val Ala Leu Gly Ser Glu Val Pro Leu Arg
        275                 280                 285

Ala Glu Gln Val His Glu Leu Ala Leu Gly Leu Glu Leu Ser Gly Ala
    290                 295                 300

Arg Phe Leu Trp Ala Leu Arg Lys Pro Thr Asp Ala Pro Asp Ala Ala
305                 310                 315                 320

Val Leu Pro Pro Gly Phe Glu Glu Arg Thr Arg Gly Arg Gly Leu Val
                325                 330                 335

Val Thr Gly Trp Val Pro Gln Ile Gly Val Leu Ala His Gly Ala Val
            340                 345                 350

Ala Ala Phe Leu Thr His Cys Gly Trp Asn Ser Thr Ile Glu Gly Leu
        355                 360                 365

Leu Phe Gly His Pro Leu Ile Met Leu Pro Ile Ser Ser Asp Gln Gly
    370                 375                 380

Pro Asn Ala Arg Leu Met Glu Gly Arg Lys Val Gly Met Gln Val Pro
385                 390                 395                 400

Arg Asp Glu Ser Asp Gly Ser Phe Arg Arg Glu Asp Val Ala Ala Thr
                405                 410                 415

Val Arg Ala Val Ala Val Glu Glu Asp Gly Arg Arg Val Phe Thr Ala
            420                 425                 430

Asn Ala Lys Lys Met Gln Glu Ile Val Ala Asp Gly Ala Cys His Glu
        435                 440                 445

Arg Cys Ile Asp Gly Phe Ile Gln Gln Leu Arg Ser Tyr Lys Ala
    450                 455                 460
```

<210> SEQ ID NO 6
<211> LENGTH: 1389
<212> TYPE: DNA
<213> ORGANISM: Artificial Sequence
<220> FEATURE:
<223> OTHER INFORMATION: HvUGT nucleotide sequence

<400> SEQUENCE: 6

```
atggacggcg acggaaacag ttcatcaagt tctagtcctc tgcatgttgt tatatgtccc     60

tggctagctc ttgggcatct tcttccttgt ttggacattg cggaaagact ggcctcaaga    120

ggacacaggg tcagcttcgt atccacgcca agaaatattg cccgtctacc cccgcttagg    180

ccagcggtgg ctcccttagt agagttcgtt gctctacctc tgcctcacgt ggacgggtta    240

cctgaagggg ctgaaagtac aaacgatgta ccctatgaca agtttgaact tcaccgtaag    300

gcgttcgacg ggctggccgc tccttttagc gagttcttga gagctgcttg tgccgagggg    360

gctggttccc gtcctgattg gctaatcgtg gatacattcc atcactgggc agcggcagcc    420

gccgttgaaa ataaagtgcc atgcgtgatg ttactgcttg gtgcagccac cgttattgcc    480

gggttcgcaa gaggggtcag tgagcacgcc gccgctgcag tcggtaaaga gagaccggcc    540

gctgaagccc cgagttttga gacggagaga cgtaaactta tgaccactca gaatgcaagt    600

ggtatgacgg ttgcagaaag gtatttccta accttaatgc gtagtgactt ggtcgcaata    660

cgtagctgcg ccgagtggga gcccgagtct gtcgcggcgt tgacaacctt agcaggcaag    720

cccgtcgttc ctttaggctt gctgccaccg tctccagagg gggggagagg cgtttccaag    780

gaggacgccg cggttcgttg gttggatgcg caacccgcga agagcgtcgt gtatgtcgcg    840
```

-continued

```
ttaggcagtg aggttccatt gagagctgaa caagtccacg agttggcgct tggtttagaa    900

ttatctggcg ctaggttttt atgggcgcta aggaaaccca ccgacgcgcc agatgccgcg    960

gtattgccgc cagggtttga ggaaaggact cgtggcagag ggcttgtcgt gaccggttgg   1020

gtgcctcaaa tcggcgttct tgctcatggt gccgtagcag cattcttgac tcattgtggc   1080

tggaattcaa ccatcgaggg gctgctgttt ggtcacccgt tgatcatgct gccaataagc   1140

tccgaccaag gacccaatgc tcgtttgatg gaaggcagaa aagtggggat gcaggtgccc   1200

agagacgaaa gcgatgggag ttttaggaga gaagatgtgg cagctactgt tcgtgctgta   1260

gcggtggagg aagatggcag aagggttttt acagctaatg cgaagaagat gcaagaaata   1320

gtagccgacg ggcttgtca cgagagatgc atcgatggat ttatccaaca actgcgttcc   1380

tacaaagct                                                           1389


<210> SEQ ID NO 7
<211> LENGTH: 31
<212> TYPE: DNA
<213> ORGANISM: Artificial Sequence
<220> FEATURE:
<223> OTHER INFORMATION: Forward primer for CYC1 terminator

<400> SEQUENCE: 7

tgattgtcga tatcatgtaa ttagttatgt c                                    31


<210> SEQ ID NO 8
<211> LENGTH: 28
<212> TYPE: DNA
<213> ORGANISM: Artificial Sequence
<220> FEATURE:
<223> OTHER INFORMATION: Reverse primer for GAL10 promoter

<400> SEQUENCE: 8

catcaattct tacttttttt ttggatgg                                        28


<210> SEQ ID NO 9
<211> LENGTH: 44
<212> TYPE: DNA
<213> ORGANISM: Artificial Sequence
<220> FEATURE:
<223> OTHER INFORMATION: Forward primer for connecting TaUGT and GAL10
      promoter

<400> SEQUENCE: 9

catccaaaaa aaaagtaaga attgatggac gacgggtctt ctag                      44


<210> SEQ ID NO 10
<211> LENGTH: 48
<212> TYPE: DNA
<213> ORGANISM: Artificial Sequence
<220> FEATURE:
<223> OTHER INFORMATION: Reverse primer for connecting TaUGT and CYC1
      terminator

<400> SEQUENCE: 10

ctaattacat gatatcgaca atcattcttt ataggacctt agctgttg                  48


<210> SEQ ID NO 11
<211> LENGTH: 44
<212> TYPE: DNA
<213> ORGANISM: Artificial Sequence
<220> FEATURE:
<223> OTHER INFORMATION: Forward primer for connecting EUGT11 and GAL10
      promoter
```

-continued

```
<400> SEQUENCE: 11

catccaaaaa aaaagtaaga attgatggac tccggctaca gttc                    44


<210> SEQ ID NO 12
<211> LENGTH: 45
<212> TYPE: DNA
<213> ORGANISM: Artificial Sequence
<220> FEATURE:
<223> OTHER INFORMATION: Reverse primer for connecting EUGT11 and CYC1
      terminator

<400> SEQUENCE: 12

ctaattacat gatatcgaca attagtcctt ataagaacgt agctg                   45


<210> SEQ ID NO 13
<211> LENGTH: 42
<212> TYPE: DNA
<213> ORGANISM: Artificial Sequence
<220> FEATURE:
<223> OTHER INFORMATION: Forward primer for connecting HvUGT and GAL10
      promoter

<400> SEQUENCE: 13

catccaaaaa aaaagtaaga attgatggac ggcgacggaa ac                      42


<210> SEQ ID NO 14
<211> LENGTH: 45
<212> TYPE: DNA
<213> ORGANISM: Artificial Sequence
<220> FEATURE:
<223> OTHER INFORMATION: Reverse primer for connecting HvUGT and CYC1
      terminator

<400> SEQUENCE: 14

ctaattacat gatatcgaca atcaagcttt gtaggaacgc agttg                   45


<210> SEQ ID NO 15
<211> LENGTH: 18
<212> TYPE: DNA
<213> ORGANISM: Artificial Sequence
<220> FEATURE:
<223> OTHER INFORMATION: Forward primer for GAL10 promoter

<400> SEQUENCE: 15

ggatccatcg cttcgctg                                                 18


<210> SEQ ID NO 16
<211> LENGTH: 20
<212> TYPE: DNA
<213> ORGANISM: Artificial Sequence
<220> FEATURE:
<223> OTHER INFORMATION: Reverse primer for CYC1 terminator

<400> SEQUENCE: 16

gcaaattaaa gccttcgagc                                               20
```

GLYCOSYLTRANSFERASE AND *STEVIOL* GLUCOSIDE PREPARATION METHOD USING SAME

TECHNICAL FIELD

The present invention relates to a glycosyltransferase and a composition and method for producing steviol glycoside using the same, and more specifically, it relates to a rebaudioside glycosyltransferase that transfers glucose to steviol glycoside, a recombinant strain expressing the enzyme, and a method for producing rebaudioside of a steviol glycoside, using the same.

RELATED ART

Sweeteners are known to be the most commonly used ingredients in the food, beverage, or confectionery industry. The sweetener can be added to the final food product in the manufacturing process, or it can be used alone with being diluted appropriately, as a table sweetener or a household substitute for sugar in baking. Sweeteners include natural sweeteners such as sucrose, high fructose corn syrup, molasses, maple syrup, and honey, and artificial sweeteners such as aspartame, saccharin, and sucralose.

Stevia extract is a natural sweetener that can be extracted from the perennial shrub, *Stevia rebaudiana*. Stevia extract is a product refined to varying degrees, used as a high-sweet seasoning in foods and blends, or sold alone as a table sweetener.

Extracts of the stevia plant contain rebaudioside and other steviol glycosides that contribute to the sweet taste, but rebaudioside A is predominantly contained in commercially-available products, and small amounts of other glycosides such as rebaudiosides C, D, and F are included. Stevia extract from plants may contain contaminants such as derivative compounds that cause off-flavors. These off-flavors can generally be problematic depending on the selected food system or application.

In addition, the composition of stevia extract can be very diverse depending on the soil and climate in which the plant grows. Depending on the source plant, climatic conditions, and extraction process, the amount of rebaudioside A in commercial manufacture is reported to vary from 20 to 97% of the total content of steviol glycosides. Other steviol glycosides are present in varying amounts in stevia extract.

Since the stevia extract produced from the stevia plant contains several steviol glycosides and compounds that cause off-flavors, and recovery and purification are labor-intensive and inefficient, there is still a need for a recombinant production system capable of accumulating steviol glycosides such as Reb D and Reb M in high yield. To this end, the enzymes with good efficiency is still need to be developed. In addition, there is still a need for improved production of Reb D for production of the steviol glycoside Reb M in recombinant hosts for commercial use.

DETAILED DESCRIPTION OF THE INVENTION

Technical Problem

An embodiment of the present invention relates to a glycosyltransferase that transfers glucose to steviol glycoside, a nucleic acid molecule encoding the enzyme protein, a recombinant vector containing the nucleic acid molecule, and a transformed microorganism.

An embodiment of the present invention relates to a composition for production of steviol glycoside comprising at least one selected from the group consisting of a glycosyltransferase protein that transfers glucose to the steviol glycoside, a recombinant microorganism expressing the enzyme protein, cells of the microorganisms, cell lysates of the microorganisms, cultures of the microorganisms, and extracts thereof.

An embodiment of the present invention relates to a method for producing steviol glycoside comprising reacting one selected from the group consisting of a glycosyltransferase protein that transfers glucose to the steviol glycoside, a recombinant microorganism expressing the enzyme protein, cells of the microorganisms, cell lysates of the microorganisms, cultures of the microorganisms, and extracts thereof, with a substrate of the enzyme.

Technical Solution

Hereinafter, the present invention will be described in more detail.

An embodiment of the present invention is a glycosyltransferase that transfers glucose to steviol glycoside, and more specifically, UDP-glucosyltransferase (i.e., uridine diphosphate glucosyltransferase, abbreviated as UGT).

The UDP-glycosyltransferase relates to an enzyme protein comprising an amino acid sequence having a sequence identity of at least 92%, at least 95%, at least 97%, at least 99%, at least 99.3% or at least 99.5% with the amino acid sequence of SEQ ID NO: 1. For example, if an amino acid sequence has the same amino acid sequence identity and exhibits an efficacy corresponding to that of the enzyme protein consisting of the amino acid sequence of SEQ ID NO: 1, even if it includes some sequences are deleted, modified, substituted or inserted, it is obviously included within the scope of the present invention. The enzyme protein can be encoded by a nucleic acid molecule having a nucleotide sequence of SEQ ID NO:2, or a nucleotide sequence having a nucleotide sequence identity of 40% or more, 50% or more, 60% or more, 70% or more, 80% or more, 90% or more, 95% or more, 97% or more, or 99% or more of It may be encoded by a nucleotide sequence that is 99% or more or 99% or more with a nucleotide sequence of SEQ ID NO: 2.

The term "homology" or "identity" as used herein refers to the degree of similarity with a given amino acid sequence or nucleotide sequence and may be expressed as a percentage. In this disclosure, a homologous sequence having the same or similar activity as a given amino acid sequence or nucleotide sequence is expressed as "% homology" or "% identity".

According to another embodiment of the present invention, an enzyme protein comprising an amino acid sequence having a sequence identity of 92% or more, 95% or more, 97% or more, or 99% or more with an amino acid sequence of SEQ ID NO: 1 includes a wild-type enzyme having a same amino acid sequence as SE ID NO: 1, and mutant enzyme proteins where some sequences are deleted, modified, substituted, or inserted, as long as they exhibit an efficacy corresponding to the protein consisting of the amino acid sequence of SEQ ID NO: 1.

The UDP-glycosyltransferase according to the present invention, has an activity of converting one or more substrates selected from the group consisting of stevioside and rebaudioside A (Reb A), into steviol glycoside, for example, rebaudioside D (Reb D) and rebaudioside E (Reb E), in the presence of a glucose donor. In more detail, the enzyme can convert Reb A to Reb D, and stevioside to Reb E (see Reaction Scheme 1 below), and has an conversion activity to a single substrate or a mixed substrate of Reb A and stevioside.

The conversion of Reb A to Reb D is a transfer of glucose through the binding of the beta 1-2 glycosidic bond on the steviol ring, and mainly occurs at position 19 of the steviol ring. Steviol glycoside can include 1 to 3 of glucose molecule bound by beta bonds.

[Reaction Scheme 1]

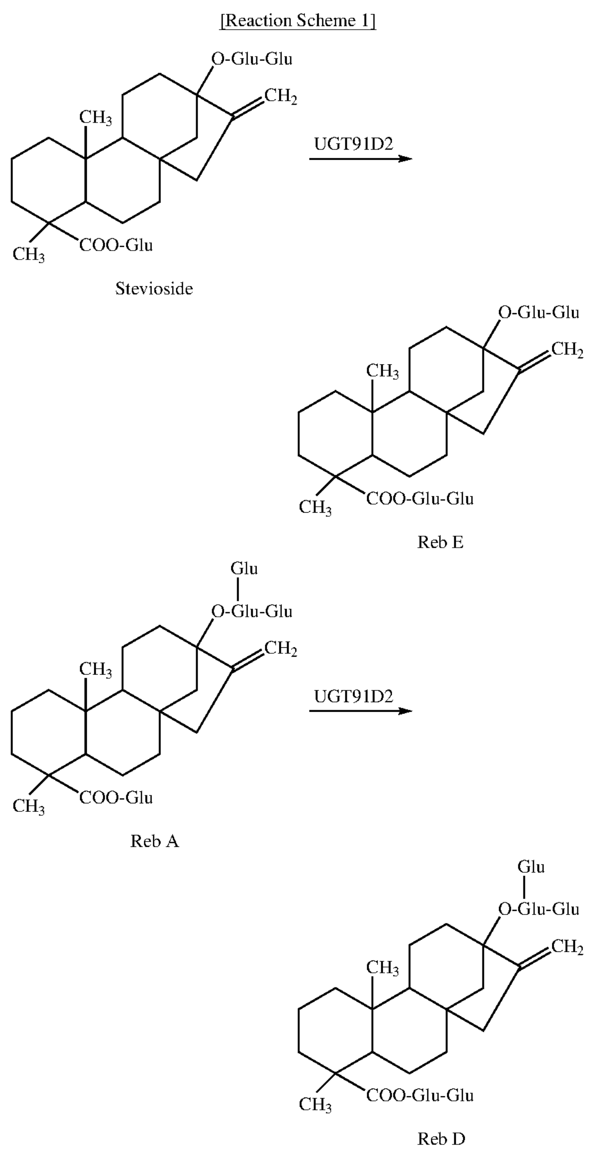

Stevioside

Reb E

Reb A

Reb D

The UDP-glycosyltransferase according to the present invention has an activity of converting more than 40% by weight of Reb A to Reb D, or more specifically 40% by weight or more, 50% by weight or more, 60% by weight or more, 65% by weight or more, or 70% by weight or more of Reb A to Reb D, in an enzymatic reaction for 2 hours to 24 hours, specifically 3 to 18 hours. In addition, the enzyme protein according to the present invention has an activity of conversion rate of Reb D having 85% or more, 90% or more, or 93% or more, for example, 85 to 110%, 90 to 110%, 93 to 110%, 85 to 100%, 90 to 100%, 93 to 100%, 85% to 99%, 90 to 99%, or 93 to 99%, based on 100% of conversion rate of Reb D for EUGT11, in an enzymatic reaction for 2 hours to 24 hours, specifically 3 to 18 hours for a single substrate of Reb A. The conversion activity of the enzyme may be measured for an enzyme reaction performed at 30° C., pH 7.2, and 150 rpm conditions for Reb A as a single substrate, and the conversion rate (%) is obtained by obtaining the peak area value analyzed by HPLC analysis method and calculating using Formula 1.

[Formula 1]

$$\text{Conversion rate of } Reb\,D(\%) = HPLC \text{ peak area of } Reb\,D/\text{whole } HPLC \text{ peak area}$$

In addition, the UDP-glycosyltransferase has an activity of converting 75% by weight or more, 80% by weight or more, 85% by weight or more, 90% by weight or more, or 95% by weight or more of mixed substrates of stevioside and Reb A, into Reb D and Reb E, in an enzymatic reaction for 2 hours to 24 hours, specifically 5 to 20 hours for the mixed substrates including stevioside and Reb A. The conversion activity of the enzyme may be measured for an enzyme reaction performed at 30° C., pH 7.2, and 150 rpm conditions for mixed substrates of stevioside and Reb A, and the conversion rate (%) is obtained by obtaining the peak area value analyzed by HPLC analysis method and calculating using Formula 2.

[Fromula 2]

$$\text{Conversion rate of } Reb\,D/E(\%) = HPLC \text{ peak area of } Reb\,D/E\,/\text{whole } HPLC \text{ peak area}$$

In addition, the enzyme protein according to the present invention has an activity of conversion rate of Reb D/E having 105% or more, 110% or more, 120% or more, 130% or more, 140% or more, or 150% or more, for examples 105% to 200%, 110% to 200%, 120% to 200%, 130% to 200%, 140% to 200%, 150% to 200%, 105% to 190%,, based on 100% of total conversion rate of Reb D/E for EUGT11, in an enzymatic reaction for 2 hours to 24 hours, specifically 5 to 20 hours for mixed substrates of stevioside and Reb A.

The enzyme protein according to the present invention does not produce or produces a very small amount of a compound having a peak corresponding to an elution time of 14.5 to 15.5 minutes in the HPLC analysis graph as a by-product. Thus, the enzyme protein according to the present invention has a higher conversion rate of Reb D/E than that of EUGT11 in a mixture containing Reb A and stevioside, and the conversion rate gradually increases as the time of enzyme reaction passes.

The UDP-glycosyltransferase according to the present invention is an enzyme (TaUGT) derived from *Triticum aestivum* in searching for plant-derived enzymes. TaUGT, found through gene search, exists as a putative protein whose function has not been clearly identified. The present inventors identified the function of this protein, and found the UGT enzyme activity, and the enzyme activity that converts stevioside and Reb A to Reb E and Reb D.

Reb D, which has high sweetness, is produced from Reb A as a saccharide present in a small amount in stevia plants, and the enzyme involved in this process is UGT91D2. An enzyme with similar activity is the EUGT11 enzyme present in rice. UGT91D2 of stevia has an activity to convert Reb A, a steviol glycoside, to Reb D, but it difficult to produce high content of Reb M due to low conversion activity.

In addition, conventionally known UGT enzymes include UGT derived from *Stevia rebaudiana*, UGT derived from rice (*Oryza sativa*) (hereinafter referred to as EUGT11), and UGT derived from barley (*Hordeum vulgare*) (hereinafter referred to as HvUGT). The UDP-glycosyltransferase according to the present invention does not produce reaction by-products compared to conventionally known EUGT11.

As a result of amino acid sequence identity analysis with HvUGT and EUGT11,the enzyme according to the present invention has 91% of amino acid sequence identity with HvUGT and 66% of amino acid sequence identity with EUGT11, and as a result of polynucleotide sequence identity analysis, the enzyme has 36% of polynucleotide sequence identify with HvUGT and 37% of polynucleotide sequence identify with EUGT11.

The UDP-glycosyltransferase according to the present invention may react in an aqueous system at a reaction temperature of 10 to 50° C. and pH 5.0 to 9.0, preferably in an aqueous system at a reaction temperature of 25 to 40° C. and pH 6.0 to 8.0, more preferably in an aqueous system at a temperature of 30° C. and a pH of 7.2. According to a preferred embodiment, the reaction can be carried out in a phosphate buffer at pH 7.2.

An embodiment of the present invention relates to a nucleic acid molecule encoding a glycosyltransferase protein that transfers glucose to steviol glycoside, a recombinant vector containing the nucleic acid molecule, and a transformed microorganism.

According to the present invention, the recombinant microorganism or cell may be a microbial cell, preferably *E. coli*, a strain of the genus *Saccharomyces*, for example, *Saccharomyces cerevisiae*, or *Pichia* yeast, but is not limited thereto.

As used herein, the term "transformation" means introducing a vector containing a nucleic acid encoding a target protein into a host cell so that the protein encoded by the nucleic acid can be expressed in the host cell. As long as the transformed nucleic acid can be expressed in the host cell, it may be inserted into and located in the chromosome of the host cell or located outside the chromosome. In addition, the nucleic acid includes DNA and RNA encoding the target protein. The nucleic acid may be introduced in any form as long as it can be introduced into a host cell and expressed. For example, the nucleic acid may be introduced into a host cell in the form of an expression cassette, which is a genetic construct containing all elements required for self-expression. The expression cassette may include a promoter operably linked to the nucleic acid, a transcription termination signal, a ribosome binding site, and a translation termination signal. The expression cassette may be in the form of an expression vector capable of self-replication. In addition, the nucleic acid may be introduced into a host cell in its own form and operably linked to a sequence required for expression in the host cell, but is not limited thereto.

In addition, the term "operably linked" as used herein means that a promoter sequence that initiates and mediates transcription of a nucleic acid encoding a target protein of the present invention and the gene sequence are functionally linked.

An example of a recombinant vector including a nucleic acid molecule encoding a glycosyltransferase protein that transfers glucose to steviol glycoside according to an embodiment of the present invention is shown in the cleavage map of FIG. 1. For example, it may include a nucleic acid molecule that encodes the enzyme according to the present invention, and a GAL10 promoter and a CYC1 terminator as transcription control sequences being operably linked to the nucleic acid molecule. The transcriptional promoters may include GAL10, GAL1, GAL2, TEF1, GPD1, and TDH3 promoters, and the transcriptional terminators may include CYC1, TEF1, and PGK1.

The method of transforming the vector in the present invention includes any method of introducing a nucleic acid into a cell, and can be performed by selecting an appropriate standard technique as known in the art according to the host cell. For example, electroporation, calcium phosphate (CaPO4) precipitation, calcium chloride (CaCl2) precipitation, microinjection, polyethylene glycol (PEG) method, DEAE-dextran method, cationic liposomal method, and lithium acetate-DMSO method, etc., but is not limited thereto.

An embodiment of the present invention is a composition for production of steviol glycoside comprising at least one selected from the group consisting of a glycosyltransferase transferring glucose to steviol glycosides, a recombinant microorganism expressing the enzyme protein, cells of the microorganisms, cell lysates of the microorganisms, cultures of the microorganisms, and extracts thereof.

The composition for production of steviol glycoside further comprises a substrate comprising at least one selected from the group consisting of stevioside and rebaudioside A, for example, steviosides, Reb A, or mixed substrates thereof. The mixed substrates are a mixture of stevioside and Reb A, or a stevia extract including steviosides or Reb A.

The composition may further include an enzyme that converts Reb D or Reb E, into Reb M, and the enzyme that converts to Reb M is a second UDP-glycosyl transferase, such as UGT76G1 derived from stevia.

The composition may further include a glucose donor, for example, UDP-glucose or a saccharide capable of generating UDP-glucose. The glycosyltransferase protein that transfers glucose to steviol glycoside according to the present invention transfers glucose from a glucose donor, to steviol glycoside.

The culture includes an enzyme produced from a microorganism producing UDP-glycosyltransferase, and may contain microbial cells, or be in a cell-free form not containing the strain. The lysate means a lysate obtained by disrupting the cells of a microorganism producing UDP-glycosyltransferase or a supernatant obtained by centrifuging the lysate, where it includes an enzyme produced from a microorganism producing the UDP-glycosyltransferase.

The culture of the strain includes an enzyme produced from a microorganism producing the UDP-glycosyltransferase, and may contain microbial cells, or be in a cell-free form not containing the microbial cells. In the present disclosure, unless otherwise specified, the microorganism producing the UDP-glycosyltransferase means including one or more selected from the cell of the microorganisms, the culture of the strain, the lysate of the cell, the supernatant of the lysate, and extracts thereof.

When steviol glycoside is produced using the composition for producing steviol glycoside, the reaction temperature and reaction pH conditions using UDP-glycosyltransferase or microorganisms producing the enzyme are as described above in the reaction temperature and reaction pH conditions of the enzyme.

An embodiment of the present invention is a method of producing steviol glycosides, comprising reacting one selected from the group consisting of a glycosyltransferase protein that transfers glucose to the steviol glycoside, a recombinant microorganism expressing the enzyme protein, cells of the microorganisms, cell lysates of the microorganisms, cultures of the microorganisms, and extracts thereof, with a substrate of the enzyme.

An embodiment of the present invention is a method of producing at least steviol glycoside selected from the group consisting of Reb D and Reb E, comprising reacting at least one selected from the group consisting of a glycosyltransferase protein that transfers glucose to the steviol glycoside, a recombinant microorganism expressing the enzyme protein, cells of the microorganisms, cell lysates of the microorganisms, cultures of the microorganisms, and extracts thereof, with at least substrate selected from the group consisting of stevioside and Reb A, in a presence of glucose donor.

A further embodiment of the present invention is a method of producing Reb M, including reacting at least one selected from the group consisting of UDP-glucosyltransferase enzyme protein of the present invention, a recombinant microorganism expressing the enzyme protein, cells of the microorganisms, cell lysates of the microorganisms, cultures of the microorganisms, and extracts thereof, with at least substrate selected from the group consisting of stevioside and Reb A, in a presence of glucose donor, and reacting the produced steviol glycoside with at least one selected from the group consisting of a second UDP-glucosyltransferase enzyme protein, a recombinant microorganism expressing the enzyme protein, cells of the microorganisms, cell lysates of the microorganisms, cultures of the microorganisms, and extracts thereof, in a presence of glucose donor.

The second UDP-glucosyltransferase enzyme protein used in the manufacturing step of Reb M may include UGT76G1 and the like.

Since the method of the present invention can significantly shorten the production cycle, improve production capacity, and provide a product with lower cost and higher purity, it can be used economically by the food and beverage industries.

The substrate of the UDP-glucosyltransferase enzyme protein according to the present invention may be a stevia extract from SINOCHEM (China), which contains 50% Reb A and contains 90% of steviol glycosides in the extract, so as to be used for performing the enzymatic conversion.

Steviol glycosides prepared by using the UDP-glucosyltransferase enzyme protein according to the present invention and a recombinant microorganism expressing the enzyme protein is a high-intensity sweetener that is added to various foods and beverages as an additive, or sold as single-component products, such as a table sweetener.

Effect of the Invention

Compared to conventionally known UGT, the UDP-glucosyltransferase enzyme protein according to the present invention has substrate specificity that acts on several steviol glycosides and has the advantage of not producing reaction by-products, the steviol glycosides can be prepared by reacting at least one substrate selected from the group consisting of the enzyme protein, a recombinant microorganism expressing the enzyme protein, cells of the microorganisms, cell lysates of the microorganisms, cultures of the microorganisms, and extracts thereof, with at least one substrate selected from the group consisting of steviosides and Reb A, in the presence of glucose donor, and the steviol glycosides can be added and used in various foods and beverages as a high-intensity sweetener.

DETAILED DESCRIPTION OF THE EMBODIMENTS

Figure 1:
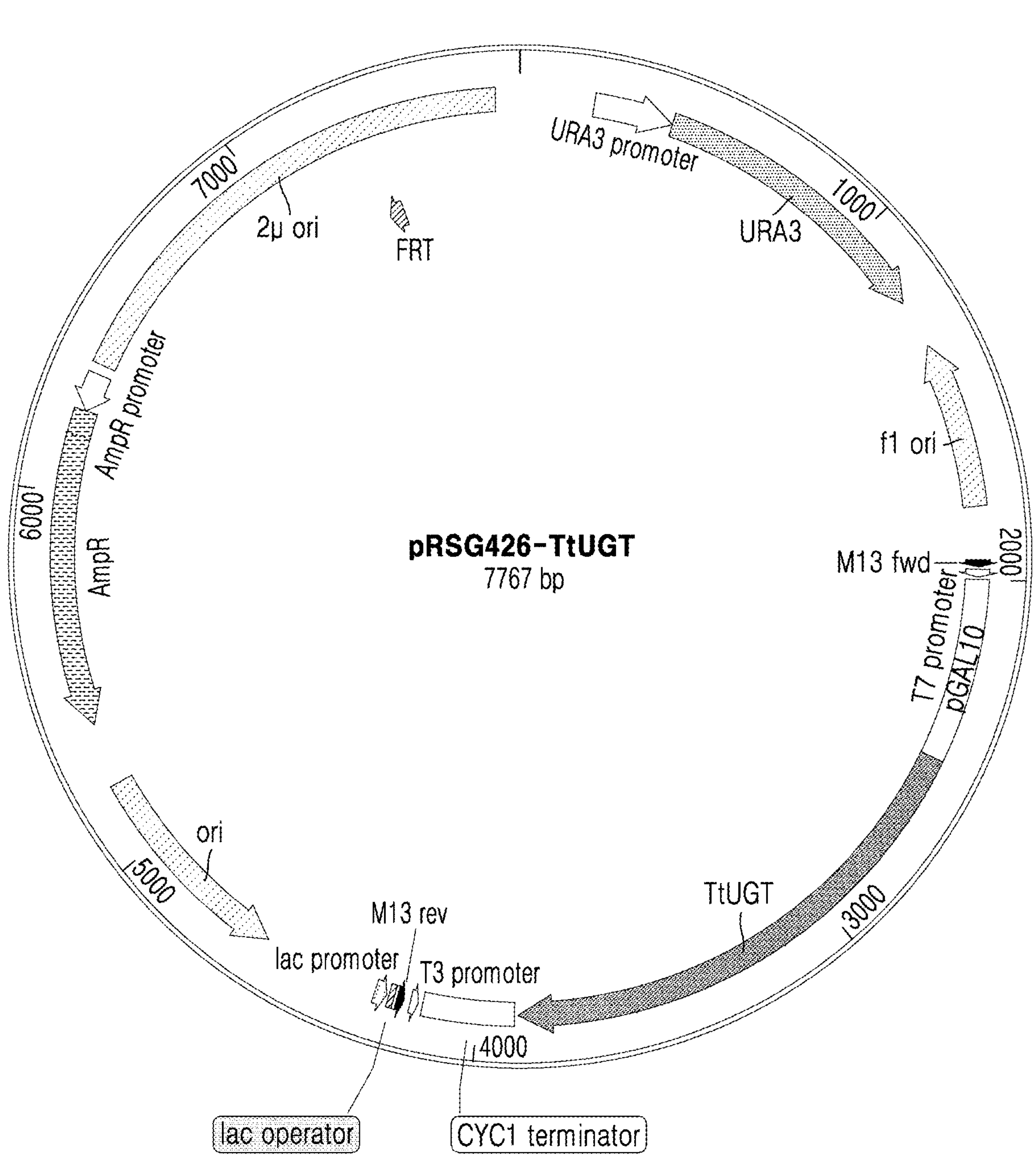
FIG. 1 is a cleavage map of a vector for preparing a yeast strain producing a glycosyltransferase according to an example of the present invention.

The present invention will be described in more detail with reference to the following examples, but the scope of the present invention is not intended to be limited to the scope of the following illustrative examples.

Example 1. Preparation of Recombinant Strain Producing Enzyme

1-1: Searching for UGT Derived From EUGT (*Oryza sativa* UGT)

In order to search and select the proteins having homology with the sequence of EUGT11 (UDP-glycosyltransferase 91C1 [*Oryza sativa* Japonica Group] (ATCC No. AAS07253.1), Blast program were used. Among the searched and selected proteins, the nucleotide sequences encoding the proteins of XP_044372292.1 (putative UDP-rhamnose: rhamnosyltransferase 1 [*Triticum aestivum*]), TVU45496.1 (hypothetical protein EJB05_04985 [*Eragrostis curvula*]), EAZ00153.1 (hypothetical protein Osl_22159 [*Oryza sativa Indica* Group]), XP_023157255.1 (uncharacterized protein of *Zea may*), RLM584514.1 (transferase, *Panicum miliaceum*, PWZ40097.1 (Soyasaponin III rhamnosyltransferase [*Zea mays*]), and RCV39092.1(hypothetical protein SETIT_8G195800v2 [*Setaria italica*]) were synthesized (Gblock synthesis).

1-2: Production of Recombinant Strain Producing Enzyme

The synthesized genes were subcloned into a plasmid capable of being expressed in *S. cerevisiae* to make a construct capable of expression.

TABLE 1

| Name | Nucleotide sequence (5'->3') | SEQ ID NO |
|---|---|---|
| Forward primer of CYC1 terminator | TGATTGTCGATATCATG TAATTAGTTATGTC | 7 |
| Reverse primer of GAL10 promoter | catCAATTCttactttt tttttggatgg | 8 |
| Forward primer of TaUGT connecting to GAL10 promoter | catccaaaaaaaaagta aGAATTGATGGACGACG GGTCTTCTAG | 9 |

TABLE 1-continued

| Name | Nucleotide sequence (5'->3') | SEQ ID NO |
|---|---|---|
| Reverse primer of TaUGT connecting to CYC1 terminator | CTAATTACATGATATCG ACAATCATTCTTTATAG GACCTTAGCTGttg | 10 |
| Forward primer of EUGT11 connecting to GAL10 promoter | catccaaaaaaaaagta aGAATTGATGGACTCCG GCTACAGTTC | 11 |
| Reverse primer of EUGT11 connecting to CYC1 terminator | CTAATTACATGATATCG ACAATTAGTCCTTATAA GAACGTAGCTG | 12 |
| Forward primer of HvUGT connecting to GAL10 promoter | catccaaaaaaaaagta aGAATTGATGGACGGCG ACGGAAAC | 13 |
| Reverse primer of HvUGT connecting to CYC1 terminator | CTAATTACATGATATCG ACAAtcaAGCTTTGTAG GAACGCAGTTG | 14 |
| Forward primer of GAL10 promoter | ggatccatcgcttcgct g | 15 |
| Reverse primer of CYC1 terminator | GCAAATTAAAGCCTTCG AGC | 16 |

The vector used to test the activity of protein was pRS426 vector including Ura auxotrophic marker (selection marker) to select the vector in S. cerevisiae, GAL10 promoter was used as a promoter, CYC1 terminator was used as a terminator. The synthesized genes were cloned into the plasmid. For cloning of the TaUGT gene, primer pairs (SEQ ID NO: 9 and SEQ ID NO: 10) were prepared to overlap the GAL10 promoter (SEQ ID NO: 7) and the CYC1 terminator (SEQ ID NO: 8), and the enzyme gene was amplified through PCR amplification and the amplified genes were subcloned through Gibson assembly (HIFi DNA master mix, NEW ENGLAND BIOLABS). The genes in the form of the subcloned plasmid were transformed into Escherichia coli (DH5a), selected and amplified, and the sequence of the amplified plasmid was analyzed to confirm that the expression gene for the enzyme was correctly subcloned. The EUGT11 gene (SEQ ID NO: 4) and the HvUGT gene (SEQ ID NO: 6), known for their activity, were synthesized (Gblock synthesis), and the genes were amplified in the same way as the TaUGT gene and cloned into pRS426 vector. To induce enzyme expression under the same conditions, the GAL10 promoter was used as the promoter and CYC1 was used as the terminator. Specifically, EUGT11 forward primer linked to the GAL10 promoter (SEQ ID NO: 11), EUGT11 reverse primer linked to the CYC1 terminator (SEQ ID NO: 12), HvUGT forward primer linked to the GAL10 promoter (SEQ ID NO: 13), and CYC1 HvUGT reverse primer (SEQ ID NO: 14) linked to the terminator was used. The cassette produced above for enzyme production are shown in Table, and Sc means *Saccharomyces cerevisiae*. As a transformation method for introducing a gene into *S. cerevisiae* CENPK2-1c (Euroscarf), 0.1 M LiAc (Lithium Acetate) was treated and introduced through heat shock. The introduced strain was selected in SC-Ura medium, and the enzyme activity of the selected colony was tested through culture.

TABLE 2

| Promoter | gene | terminator | gene origin |
|---|---|---|---|
| ScGAL10 | EUGT11 | ScCYC1 | *Oryza sativa* |
| ScGAL10 | TaUGT | ScCYC1 | *Triticum aestivum* |
| ScGAL10 | EcUGT | ScCYC1 | *Eragrostis curvular* |
| ScGAL10 | OsiUGT | ScCYC1 | *Oryza sativa indica* |
| ScGAL10 | HvUGT | ScCYC1 | *Hordeum vulgare* |

The six recombinant plasmids prepared above were transformed into *S. cerevisiae* CENPK2-1c (Euroscarf) strain. Recombinant strains into which six gene cassettes were inserted were selected using selectable markers in SC-Ura solid medium (SC-Ura medium +2% agar). The composition of the SC-Ura solid medium included YNB 6.7 g/L, Drop out mix 0.7 g/L, glucose D50 g/L and agar 20 g/L, and was adjusted to pH 6.0.

Example 2. Culture of Recombinant Strain

The yeasts transformed with the plasmid prepared in Example 1 were selected in synthetic complete (SC) medium using URA-drop out mix, and the selected yeasts were induced to express the enzyme through liquid culture.

Specifically, colonies selected from the SC-Ura solid medium were inoculated into a test tube containing 3 mL of SC-Ura liquid medium and cultured overnight. The concentration of the cultured cells was confirmed by measuring the OD600 absorbance, and inoculated into a 250 mL flask containing 25 mL of SC-Ura liquid medium so that the OD600 absorbance finally reached 0.1 (final) and cultured for 24 hours (30° C., 240 rpm).

In order to induce enzyme expression in the primary cultured cells, an equal amount of YPG medium was added and secondary culture was performed for 24 hours. The secondary cultured cells were collected by centrifugation (4,000 rpm, 10 min). The SC-Ura liquid medium included YNB (yeast nitrogen base) 6.7 g/L, Drop-out mix 0.7 g/L, Glucose 50 g/L, MES 50 mM and the pH of the medium was adjusted to 6.0 using NaOH. The YPG medium included Bacto-peptone 20g/L, Yeast Extract 10g/L, Galactose 20g/L, and Phosphate buffer (sodium salt) 100 mM, and the pH of the medium was adjusted to 6.0.

Example 3. Evaluation of Enzyme activity

The cells from the culture of the recombinant strain obtained in Example 2 were recovered by centrifugation (4,000 rpm, 10 min). 10 mL of the recovered cells were collected and washed twice with the same amount of water. After resuspending the washed cells in 100 mM phosphate buffer (pH 7.2) so that the OD600 value was 100, 100 mg of glass beads (Sigma) having a diameter of 0.4 to 0.6 mm were placed in a cap tube, and added with 100 mM 1 ml of phosphate buffer (pH 7.2). The cells were repeatedly disrupted 5 times for 30 seconds in a bead beater. The cell disruption solution was centrifuged (13,000 rpm, 15 min) in a refrigerated state to obtain a supernatant as a crude enzyme solution.

The reaction solution for enzyme activity evaluation included substrate Reb A (95%, Sinochem), MgCl2 and UDP-Glucose, and was added with 0.1 mL of the crude enzyme solution to prepare a total reaction volume of 0.5 mL, and the substrate Reb A (95%, Sinochem) was 2 g/L, MgCl2 3 mM, and UDP-Glucose 4 mM in the final reaction solution. The enzyme reaction was performed on the prepared reaction solution at a temperature of 30° C., pH 7.2 and 150 rpm, and samples were taken at 3 hours and 18 hours after the start of the reaction, respectively, to test the degree of reaction according to the rebound time.

The enzyme reaction was quenched by boiling the enzyme reaction solution for 5 minutes, and the obtained supernatant by centrifuging (13,000 rpm, 10 min) was analyzed to test the enzyme reaction product. Specifically, the analysis of the enzymatic reaction product was analyzed using HPLC-Chromatography to confirm the conversion rate of the product. Since the crude enzyme solution obtained from the cell lysate of the recombinant strain showed activity to convert Reb A to Reb D, the activity was measured by measuring the production rate of Reb D.

Specifically, the column used for HPLC analysis of the conversion product was UG120 (C18 250 mm× 46 mm, 5 um 110 A particle, Shiseido), and analysis was performed at 210 nm. As a mobile phase, water containing 0.01% TFA (Trifluoroacetic acid, Sigma) and acetonitrile were analyzed using a gradient, and the mobile phase was flowed at 1 mL/min and analyzed for a total of 40 minutes. The conditions of HPLC analysis are shown in Table 3 below. A graph of HPLC analysis of the conversion product is shown in Table 4. The conversion rate of Reb D for the enzyme shown in Table 4, which converts the Reb A as a single substrate into Red D, is calculated according to Formula 1 below, and the relative conversion rate of Reb D by the enzyme means conversion rate of Reb D with TaUGT or HvUGT enzyme converted, which is based on the 100% of conversion rate of Reb D with EUGT11.

The conversion rate of Reb D by the enzyme shown in Table 4, which converts Reb A into Red D is calculated below according to Formula 1. The relative conversion rate of Reb D by the enzyme means conversion rate of Reb D with TaUGT or HvUGT, which is based on the 100% conversion rate of Reb D with EUGT11.

[Formula 1]

$$\text{Conversion rate of } Reb\,D(\%) = HPLC \text{ peak area of } Reb\,D/\text{whole } HPLC \text{ peak area}$$

TABLE 3

| Time (min) | Eluent A(%) | Eluent B(%) |
|---|---|---|
| 0 | 80 | 20 |
| 10 | 80 | 20 |
| 12 | 65 | 35 |
| 30 | 0 | 100 |
| 32 | 80 | 20 |
| 40 | 80 | 20 |

TABLE 4

| Enzyme name | Reaction time(hour) | Conversion rate of Reb D (%) | Relative conversion rate of Reb D (%) |
|---|---|---|---|
| EUGT11 | 3 | 45.8 | 100% |
| TaUGT | 3 | 43.4 | 94.8% |
| HvUGT | 3 | 32.5 | 71.0% |
| EUGT11 | 18 | 70.6 | 100% |
| TaUGT | 18 | 68.0 | 96.3% |
| HvUGT | 18 | 62.2 | 88.1% |

As shown in Table 4, in the conversion rate through the enzymatic reaction, the activities of EcUGT and OsiUGT were not confirmed in the initial 3-hour reaction result, a putative protein of TaUGT converted Reb A to Reb D by 40-45% which was similar to EUGT11, and it was confirmed that the enzyme had an activity improvement of about 30% compared to HvUGT (30-35% conversion). In addition, as a result of analyzing the amount of Reb D produced in the enzyme reaction solution for 18 hours, the order of conversion rate of the three enzymes showed a similar tendency to that of the 3-hour reaction.

Example 4. Enzyme Reaction Using Mixed Substrates

In the case of enzymatic activity evaluation using Reb A as in Example 3, the conversion from Reb A to only Reb D clearly confirmed the activity of the enzyme. However, since the mixed substrates were used in actual industrial production, a conversion reaction was performed on the mixed substrates containing stevioside and Reb A to evaluate the feasibility of the enzyme for industrial use using the mixed substrates. That is, when the mixed substrates are used, stevioside is converted to Reb E and Reb A is converted to Reb D.

To evaluate the enzymatic activity on the mixed substrates, RA40 (SinoChem) was used as the mixed substrates. In order to measure the exact contents of Red A and stevioside (STE) contained in the used RA 40, the HPLC analysis method was performed as substantially the same as the method described in Example 3, and the HPLC area value ratio of RebA: STE was 48:52. The enzyme used was a crude enzyme solution of TaUGT and EUGT11, which showed high activity in Example 3.

The reaction solution for evaluating enzyme activity using a mixed substrate included RA40 reaction substrate (90% by weight purity), MgCl2 and UDP-Glucose, and 0.1 mL each of TaUGT and EUGT11 crude enzyme solution according to Example 3 were added thereto to prepare a total reaction volume of 0.5 mL, and In the final reaction solution, 5 g/L of RA40 reactive substrate, 3 mM of MgCl2, and 20 mM of UDP-Glucose were added. The enzyme reaction was performed on the prepared reaction solution at a temperature of 30° C., pH 7.2, and 150 rpm, and samples were taken at 5 hours and 20 hours after the start of the reaction, respectively, to test the degree of reaction according to the reaction time. In substantially the same manner as in Example 3, the conversion product was analyzed by HPLC analysis.

Figure 2:
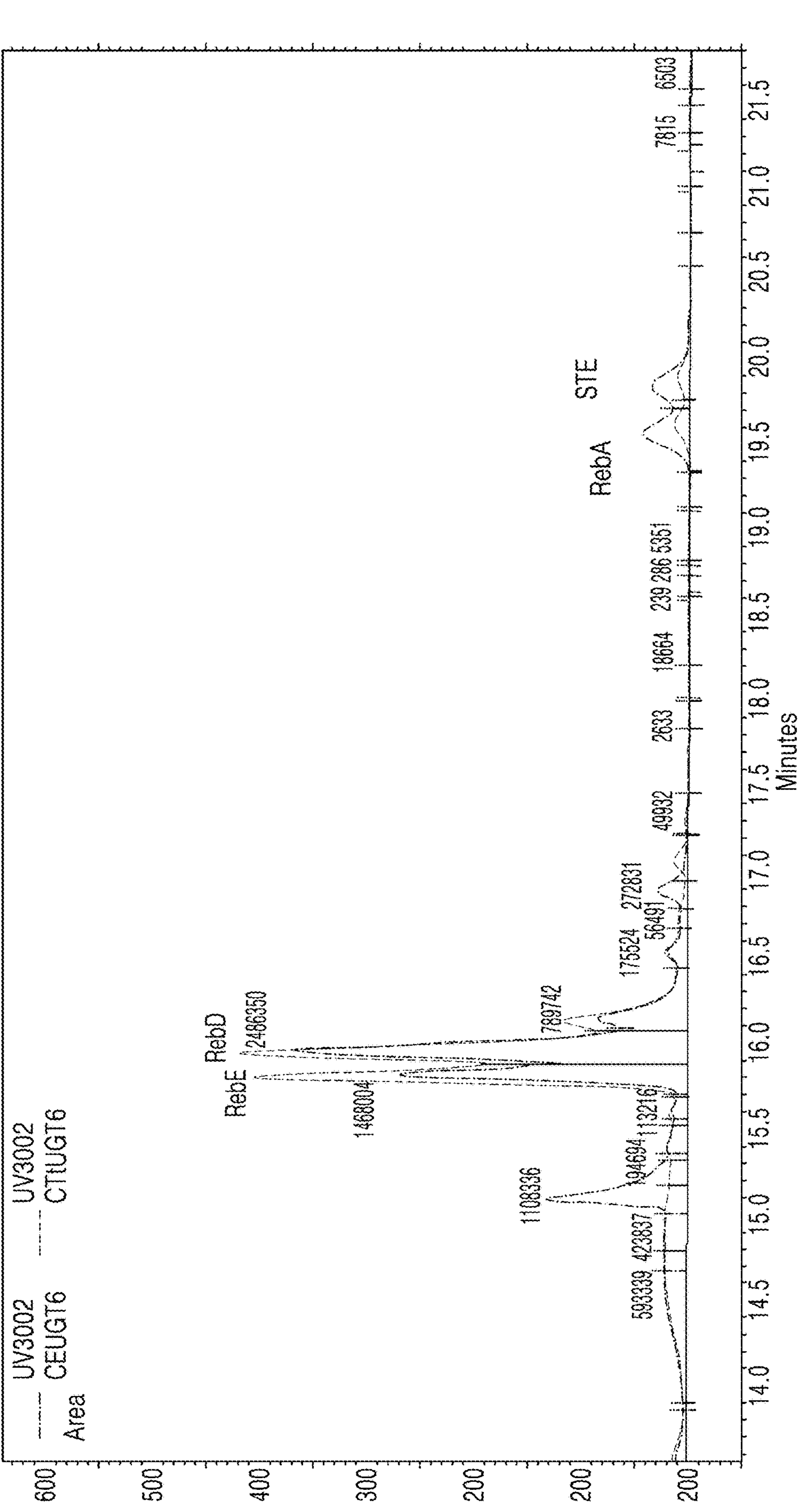
FIG. 2 shows a graph of HPLC analysis for the reaction products obtained by reacting for 5 hours mixed substrates with a glycosyltransferase according to an embodiment of the present invention.
Figure 3:
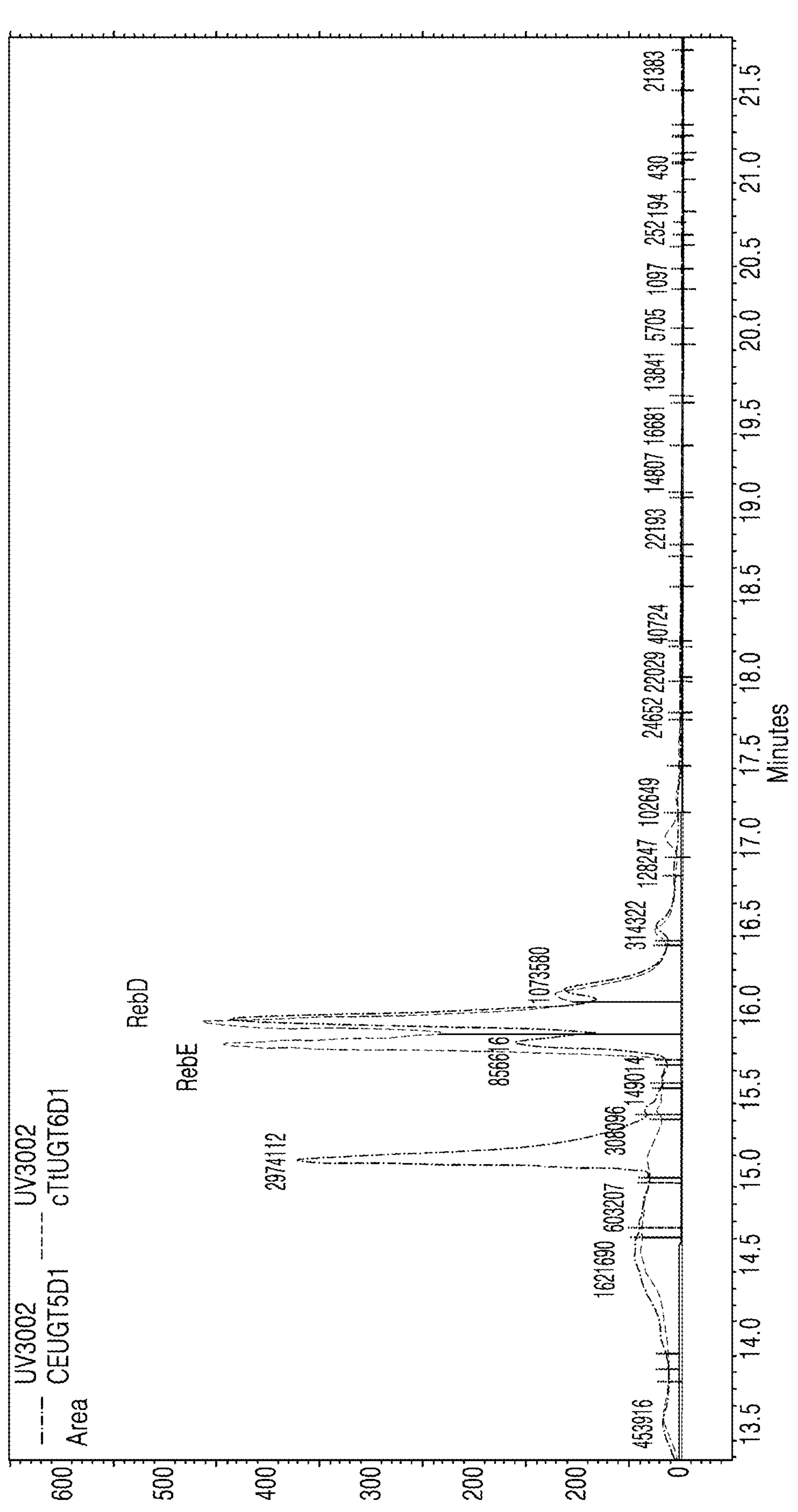
FIG. 3 shows a graph of HPLC analysis for the reaction products obtained by reacting for 20 hours mixed substrates with a glycosyltransferase according to an embodiment of the present invention.

The conversion rate of Reb D/E for the enzyme converting to Reb D/E for the RA40 mixed substrate shown in Table 5 below was calculated according to Formula 2 below, and the relative total conversion rate of Reb D/E for the enzyme means total conversion rate of Reb D/E for TaUGT or HvUGT enzyme converted based on the 100% of total conversion rate of Reb D/E for EUGT11. The analysis results of the 5-hour enzymatic reaction are shown in FIG. 2, and the analysis results of the 20-hour enzymatic reaction are shown in FIG. 3.

[Formula 2]

$$\text{Conversion rate of } Reb\,D/E(\%) = HPLC \text{ peak area of } Reb\,D/E\,/\text{whole } HPLC \text{ peak area}$$

TABLE 5

| Enzyme | Reaction time(hour) | Conversion rate for Reb D/E(%) | Relative conversion rate for Reb D/E(%) |
|---|---|---|---|
| EUGT11 | 5 | 70.0 | 100 |
| TaUGT | 5 | 92.6 | 130 |
| EUGT11 | 20 | 72.0 | 100 |
| TaUGT | 20 | 100.0 | 138 |

In the enzymatic reaction results of FIG. 2, as a result of the 5-hour conversion reaction using the RA40 substrate, blue line in a chromatogram of the HPLC result shows the reaction of TaUGT, and black line in a chromatogram of the HPLC result shows the reaction of EUGT11. According to this result, TaUGT converted RA40 substrate to Reb E and Reb D, with no production of by-products. However, EUGT11 shows a ratio of 16% in the HPLC area of the by-product at 15.1 minutes. Therefore, the overall conversion rate of Reb E and D were reduced. This suggests the occurrence of side reaction in the Reb E product. In the enzymatic reaction results of FIG. 3, as a result of the 20-hour conversion reaction using RA40 substrate, gray line in a chromatogram of the HPLC result shows the reaction of TaUGT, and black line in a chromatogram of the HPLC result shows the reaction of EUGT11. According to this result, Reb E and Reb D were produced when the RA40 substrate was consumed and converted by TaUGT. However, in the case of EUGT11, the HPLC area of the by-product at 15.1 minutes occupied a high rate of 28%. In the case of EUGT11, it was confirmed that a side reaction of Reb E produced by conversion from stevioside occurred to produce a by-product.

Therefore, the TaUGT enzyme according to the present invention has a high converstion rate of Reb D for Reb A as a single substrate and is superior to HvUGT. Moreover, for mixed substrates containing Reb A and stevioside, the total conversion rate (%) of Reb D/E is higher than EUGT11 but also increases as the enzyme reaction time pass, making it very useful, because it can produce high content of Red D/E as a substrate for industrially production of steviol glycoside, for example, Reb M.

The invention claimed is:

1. A method for producing rebaudioside D and rebaudioside E from mixed substrates comprising rebaudioside A and stevioside comprising reacting, in the presence of glucose donor, at least one selected from the group consisting of an enzyme protein, a recombinant microorganism expressing the enzyme protein, cells of the microorganism, cell lysates of the microorganism, cultures of the microorganism, and extracts thereof, with the mixed substrates comprising rebaudioside A and stevioside, wherein the enzyme protein comprises an amino acid sequence having at least 92% of sequence identity with SEQ ID NO: 1 and has uridine disphosphate-glycosyltransferase (UDP-glucoslyltransferase) activity of transferring glucose to rebaudioside A and stevioside.

2. The method according to claim 1, further comprising reacting, in the presence of glucose donor, the rebaudioside D and rebaudioside E produced by the method according to claim 1 with at least one selected from the group consisting of a second enzyme protein, a recombinant microorganism expressing the second enzyme protein, cells of the microorganism, cell lysates of the microorganism, cultures of the microorganism, and extracts thereof, wherein the second enzyme protein converts rebaudioside D or rebaudioside E into rebaudioside M.

3. The method according to claim 1, wherein the enzyme protein is obtained from *Triticum aestivum*.

4. The method according to claim 1, wherein the enzyme protein has an activity of converting 40% by weight or more of rebaudioside A to rebaudioside D in an enzymatic reaction for 2 to 24 hours.

5. The method according to claim 1, wherein the enzyme protein has conversion rate of Reb D/E is 105% to 200%, based on 100% conversion rate of Reb D/E for EUGT11, in an enzymatic reaction for 2 to 24 hours and mixed substrates containing rebaudioside A and stevioside.

6. The method according to claim 1, wherein the enzyme protein comprises the amino acid sequence of SEQ ID NO: 1.

7. The method according to claim 1, wherein the microorganism is selected from the group consisting of *Escherichia coli*, microorganism of the genus *Saccharomyces*, and microorganism of the genus *Pichia*.

* * * * *